US00PP26100P2

(12) United States Plant Patent
Guillen

(10) Patent No.: US PP26,100 P2
(45) Date of Patent: Nov. 17, 2015

(54) ***IMPATIENS* PLANT NAMED 'BALBOUCHER'**

(50) Latin Name: *Impatiens×hybrida*
Varietal Denomination: Balboucher

(71) Applicant: Ball Horticultural Company, West Chicago, IL (US)

(72) Inventor: Mario Guillen, Dulce Nombre de Cartago (CR)

(73) Assignee: Ball Horticultural Company, West Chicago, IL (US)

( * ) Notice: Subject to any disclaimer, the term of this patent is extended or adjusted under 35 U.S.C. 154(b) by 103 days.

(21) Appl. No.: 13/999,691

(22) Filed: Mar. 17, 2014

(51) Int. Cl.
*A01H 5/00* (2006.01)

(52) U.S. Cl.
USPC ..... Plt./317

(58) Field of Classification Search
USPC ..... Plt./317
See application file for complete search history.

*Primary Examiner* — Annette Para
(74) *Attorney, Agent, or Firm* — Audrey Charles

(57) ABSTRACT

A new and distinct cultivar of *Impatiens* plant named 'Balboucher', characterized by its dark cherry-red colored flowers, medium green-colored foliage, and moderately vigorous, compact, mounded-spreading growth habit, is disclosed.

1 Drawing Sheet

Latin name of genus and species of plant claimed: *Impatiens×hybrida.*

Variety denomination: 'Balboucher'.

BACKGROUND OF THE INVENTION

The present invention relates to a new and distinct cultivar of *Impatiens* plant botanically known as *Impatiens×hybrida* and hereinafter referred to by the cultivar name 'Balboucher'.

The new cultivar originated in a controlled breeding program in Cartago, Costa Rica during December 2010. The objective of the breeding program was the development of *Impatiens* cultivars that perform well under both sun and shade conditions and have a moderately vigorous, compact, mounded-spreading growth habit.

The new *Impatiens×hybrida* cultivar is the result of cross-pollination. The female (seed) parent of the new cultivar is the proprietary *Impatiens flaccida* breeding selection coded N81622, not patented, characterized by its light orchid-colored flowers, medium green-colored foliage, and vigorous, prostrate growth habit. The male (pollen) parent of the new cultivar is the proprietary *Impatiens hawkeri* breeding selection N784, not patented, characterized by its dark red-colored flowers, medium green-colored foliage, and moderately vigorous, mounded growth habit. The new cultivar was discovered and selected as a single flowering plant within the progeny of the above stated cross-pollination during April 2011 in a controlled environment in Cartago, Costa Rica.

Asexual reproduction of the new cultivar by terminal stem cuttings since April 2011 in Cartago, Costa Rica, Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balboucher' as a new and distinct cultivar of *Impatiens* plant:

1. Dark cherry-red colored flowers;
2. Medium green-colored foliage; and
3. Moderately vigorous, compact, mounded-spreading growth habit.

Plants of the new cultivar differ from plants of the female parent primarily in having a different flower color, larger leaf size, larger flower size and a more mounded growth habit. Plants of the new cultivar differ from plants of the male parent primarily in having a different flower color, smaller leaf size, smaller flower size and a more spreading growth habit.

Of the many commercially available *Impatiens* cultivars, the most similar in comparison to the new cultivar is SUNPATIENS Compact Magenta 'SAKIMP016', U.S. Plant Pat. No. 21,769. However, in side by side comparisons, plants of the new cultivar differ from plants of 'SAKIMP016' in at least the following characteristics:

1. Plants of the new cultivar have more main branches than plants of 'SAKIMP016';
2. Plants of the new cultivar have leaves that are smaller than and lighter colored than plants of 'SAKIMP016'; and
3. Plants of the new cultivar have a flower color slightly different from plants of 'SAKIMP016'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balboucher'. The plants were grown in 4.5-inch pots for 10 weeks in a greenhouse in West Chicago, Ill.

DETAILED BOTANICAL DESCRIPTION

Figure 1:
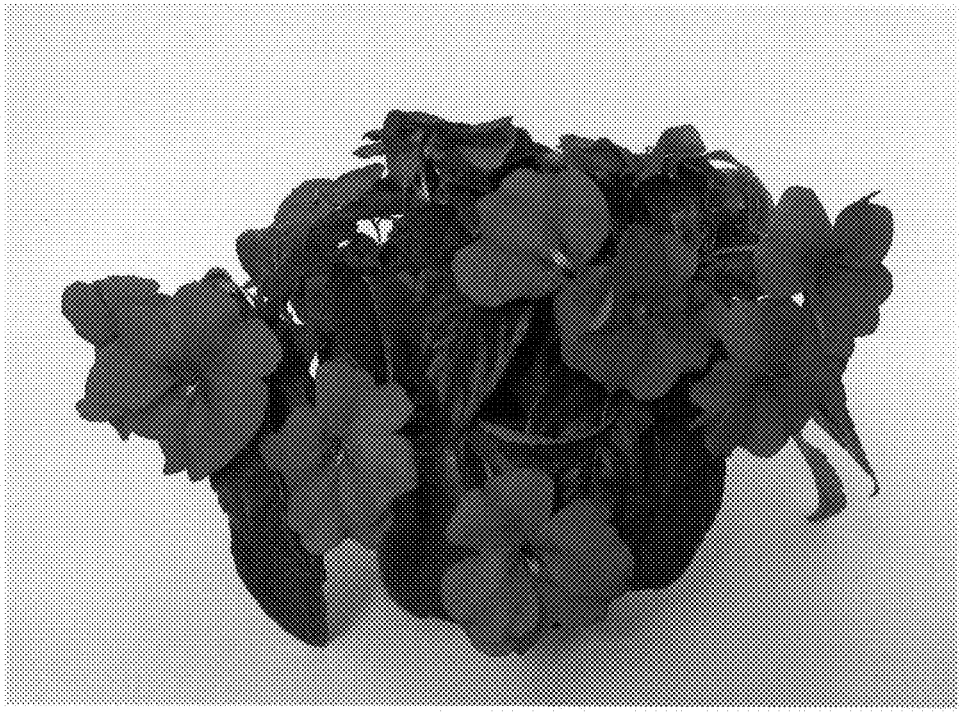
FIG. 1 illustrates a side view of the overall growth and flowering habit of 'Balboucher'.
Figure 2:
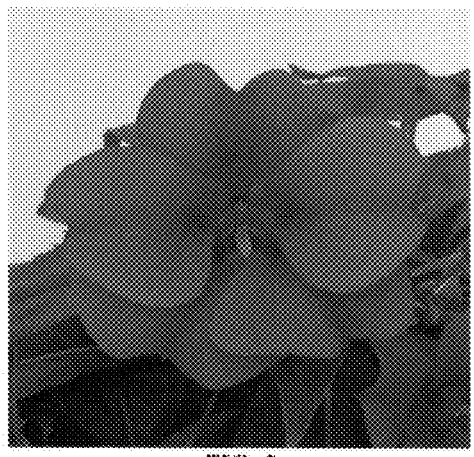
FIG. 2 illustrates a close-up view of an individual flower of 'Balboucher'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in February 2014 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 10 weeks utilizing a soilless growth medium. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Impatiens×hybrida* cultivar Balboucher.

Parentage:

*Female parent*.—Proprietary *Impatiens×flaccida* breeding selection coded N81622, not patented.

*Male parent*.—Proprietary *Impatiens hawkeri* breeding selection N784, not patented.

Propagation:

*Type cutting*.—Terminal stem.

*Time to initiate roots*.—Approximately 6 to 9 days.

*Time to produce a rooted cutting*.—Approximately 24 to 28 days.

*Root description*.—Fibrous.

*Rooting habit*.—Freely branching.

Plant description:

*Commercial crop time*.—Approximately 6 to 8 weeks from a rooted cutting to finish in a 10 cm pot.

*Growth habit and general appearance*.—Moderately vigorous, compact, mounded-spreading growth habit.

*Size*.—Height from soil level to top of plant plane: Approximately 14.0 cm. Width: Approximately 25.5 cm.

*Branching habit*.—Freely branching. Quantity of main branches per plant: Approximately 5.

*Branch*.—Strength: Moderately strong. Length: Approximately 8.5 cm. Diameter at central internode: Approximately 5.0 mm. Length of central internode: Approximately 3.4 cm. Texture: Glabrous. Color of young and mature stems: Closest to 146B with a faint overlay of 187B.

Foliage description:

*General description*.—Quantity of leaves per main branch: Approximately 6. Fragrance: None. Form: Simple. Arrangement: Whorled with up to 5 leaves per node, opposite if only two leaves at one node.

*Leaves*.—Aspect: Petiole is at an acute angle to stem and leaves are perpendicular to an obtuse angle to stem. Shape: Elliptic. Margin: Serrulate, ciliate. Apex: Acuminate. Base: Attenuate. Venation pattern: Pinnate. Length of mature leaf at center of stem: Approximately 11.0 cm. Width of mature leaf at center of stem: Approximately 4.3 cm. Texture of upper and lower surfaces: Glabrous. Color of upper surface of young and mature foliage: Closest to 137A with venation of 147B. Color of lower surface of young and mature foliage: Closest to 191A and venation of 147B.

*Petiole*.—Length: Approximately 1.5 cm. Diameter: Approximately 3.0 mm. Texture: Glabrous. Color: 147C with a faint overlay of 187C.

Flowering description:

*Flowering habit*.—'Balboucher' is freely flowering under outdoor growing conditions with substantially continuous blooming from spring through autumn and year-round in greenhouse environment.

*Lastingness of individual flower on the plant*.—Approximately 7 to 9 days.

Flower description:

*General description*.—Type: Single. Quantity per plant: Approximately 8. Fragrance: None.

*Bud*.—Rate of opening: Generally takes 1 to 2 days for bud to progress from first color to fully open flower. Quantity showing color per plant: Approximately 2.

*Bud just before opening*.—Shape: Ovoid. Length: Approximately 1.7 cm. Diameter: Approximately 1.1 cm. Color: 64A to 64B.

*Corolla*.—Shape: Round, cupped when first open with petals becoming flat with age. Diameter: Approximately 5.8 cm. Depth: Approximately 1.2 cm. Borne: Above the foliage.

*Petals*.—Quantity: 5. Shape: Obovate. Aspect: Flat. Appearance: Dull. Margin: Entire. Apex: Emarginate. Base of upper petal: Truncate. Base of lateral and lower petals: Attenuate. Length of upper petal: Approximately 2.4 cm. Width of upper petal: Approximately 3.7 cm. Length of lateral petals: Approximately 2.8 cm. Width of lateral petals: Approximately 2.6 cm. Length of lower petals: Approximately 3.4 cm. Width of lower petals: Approximately 3.2 cm. Texture of upper and lower surfaces: Glabrous. Color of upper surface when first and fully open: Upper petal closest to 71B with a heavy overlay of N66A. Lateral and lower petals closest to 71B with a heavy overlay of N66A and N81B at base. Color of lower surface when first and fully open: Closest to 64C.

*Spur*.—Quantity: 1 per flower. Length: Approximately 4.0 cm. Diameter at proximal end: Approximately 2.0 mm. Diameter at distal end: Less than 1.0 mm. Texture: Glabrous. Color: 185C with 145B at tip.

*Peduncle*.—Strength: Moderately strong. Aspect: Acute angle to stem. Length: Approximately 4.5 cm. Diameter: Approximately 2.0 mm. Texture: Glabrous. Color: 145B with a faint overlay of 187C.

*Sepals*.—Quantity per flower: 4 with one fused to base of upper petal. Sepal arrangement: 1 spurred lower sepal located between 2 side (lateral) sepals. Shape of lateral sepals: Ovate. Shape of lower sepal: Ovate. Apex of all sepals: Acuminate. Length of lateral sepals: Approximately 1.5 cm. Width of lateral sepals: Approximately 6.0 mm. Length of lower sepal: Approximately 1.8 cm. Width of lower sepal: Approximately 1.1 mm. Texture of upper and lower surfaces of all sepals: Glabrous. Color of upper and lower surfaces of lateral sepals: NN155B with an overlay of 146B and tips of 146A. Color of upper and lower surfaces of lower sepal: NN155B with an overlay of 71B and tip of 146B.

*Reproductive organs*.—Androecium: Stamen quantity: 5 per flower, fused around pistil at apex. Anther shape: Hooded. Anther length: Approximately 2.0 mm. Anther color: 71B. Filament color: 71B. Pollen amount: Sparse. Pollen color: 155D. Gynoecium: Pistil quantity: 1 per flower. Pistil length: Approximately 4.0 mm. Stigma shape: 5-pointed star. Stigma color: Colorless, transparent. Style color: 146A, darkens to 137A with age. Ovary texture: Glabrous. Ovary color: 146B, darkens to 137A with age.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balboucher', substantially as herein shown and described.

* * * * *